United States Patent
Rauniyar et al.

(10) Patent No.: US 10,933,223 B2
(45) Date of Patent: Mar. 2, 2021

(54) ACCESS DEVICES AND ASSOCIATED METHODS

(71) Applicant: Boston Scientific Scimed, Inc., Maple Grove, MN (US)

(72) Inventors: Niraj P. Rauniyar, Plymouth, MN (US); Brian P. Watschke, Minneapolis, MN (US); Timothy P. Harrah, Cambridge, MA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 459 days.

(21) Appl. No.: 15/720,923

(22) Filed: Sep. 29, 2017

(65) Prior Publication Data

US 2018/0093076 A1 Apr. 5, 2018

Related U.S. Application Data

(60) Provisional application No. 62/402,555, filed on Sep. 30, 2016.

(51) Int. Cl.
*A61M 25/06* (2006.01)
*A61B 17/34* (2006.01)
*A61B 34/10* (2016.01)
*A61B 17/00* (2006.01)
*A61B 90/00* (2016.01)

(52) U.S. Cl.
CPC ....... *A61M 25/065* (2013.01); *A61B 17/3403* (2013.01); *A61B 17/3415* (2013.01); *A61B 17/00234* (2013.01); *A61B 2017/00526* (2013.01); *A61B 2017/3407* (2013.01);

(Continued)

(58) Field of Classification Search
CPC .......... A61B 17/00234; A61B 17/3403; A61B 17/3415; A61B 2017/00526; A61B 2017/3407; A61B 2034/108; A61B 2090/037; A61B 2025/0681; A61M 25/065

See application file for complete search history.

(56) References Cited

U.S. PATENT DOCUMENTS 3,021,842 A 2/1962 Flood
3,487,837 A 1/1970 Petersen
(Continued)

FOREIGN PATENT DOCUMENTS

DE 202015003206 U1 5/2016
WO WO 2012/058349 A2 5/2012
WO WO 2016/034973 A1 3/2016

OTHER PUBLICATIONS

International Search Report and Written Opinion in corresponding International Application No. PCT/US2017/054476, dated Dec. 20, 2017 (14 pages).

*Primary Examiner* — Mohamed G Gabr
(74) *Attorney, Agent, or Firm* — Bookoff McAndrews, PLLC

(57) ABSTRACT

Aspects of access devices and methods are disclosed. One aspect of this disclosure is a device. The device may comprise: a needle guide body extending along a central axis between a distal end and a proximal end, a needle guide lumen extending through the distal and proximal ends of the needle guide body along the central axis, and a base monolithically attached to the needle guide body to define a non-variable patient-specific insertion path. Additional devices and methods are disclosed.

20 Claims, 8 Drawing Sheets

(52) U.S. Cl.
CPC ... *A61B 2034/108* (2016.02); *A61B 2090/037* (2016.02); *A61M 2025/0681* (2013.01)

(56) References Cited

U.S. PATENT DOCUMENTS

| | | | |
|---|---|---|---|
| 3,900,026 A | 8/1975 | Wagner | |
| 4,392,854 A | 7/1983 | Ibach | |
| 4,519,793 A | 5/1985 | Galindo | |
| 4,608,977 A | 9/1986 | Brown | |
| 4,675,006 A | 6/1987 | Hrushesky | |
| 4,883,053 A | 11/1989 | Simon | |
| 5,201,742 A | 4/1993 | Hasson | |
| 5,309,913 A | 5/1994 | Kormos et al. | |
| 6,159,221 A | 12/2000 | Chakeres | |
| 6,195,577 B1 | 2/2001 | Truwit et al. | |
| 6,533,792 B2 | 3/2003 | Menne et al. | |
| 6,533,794 B2 | 3/2003 | Chakeres | |
| 8,308,740 B2 | 11/2012 | Tolley et al. | |
| 2003/0114862 A1 | 6/2003 | Chu et al. | |
| 2004/0260312 A1 | 12/2004 | Magnusson et al. | |
| 2006/0089626 A1 | 4/2006 | Vlegele et al. | |
| 2006/0167416 A1* | 7/2006 | Mathis | A61B 10/0275 604/164.01 |
| 2010/0042111 A1 | 2/2010 | Qureshi et al. | |
| 2012/0041445 A1* | 2/2012 | Roose | A61B 17/1746 606/96 |
| 2013/0066192 A1 | 3/2013 | Sarvestani et al. | |
| 2013/0066232 A1 | 3/2013 | Schoepp | |
| 2013/0066334 A1 | 3/2013 | Schoepp | |
| 2013/0274778 A1 | 10/2013 | Mercier et al. | |
| 2014/0275979 A1 | 9/2014 | Fujimoto et al. | |
| 2016/0038252 A1* | 2/2016 | Barth, Jr. | A61B 34/25 600/424 |
| 2016/0228147 A1 | 8/2016 | Darrow et al. | |

* cited by examiner

300

┌─────────────────────────────────────────────────────────────┐
│ Step 350: REMOVING THE NEEDLE FROM THE CAVITY ALONG THE     │
│                         GUIDEWIRE                           │
└─────────────────────────────────────────────────────────────┘
                              ⬇
┌─────────────────────────────────────────────────────────────┐
│ Step 352: REMOVING THE NEEDLE GUIDE BODY 20 FROM THE BASE 30│
│                   ALONG THE GUIDEWIRE (352)                 │
└─────────────────────────────────────────────────────────────┘

┌─────────────────────────────────────────────────────────────┐
│ Step 360: MOVING A PROXIMAL END OF A GUIDEWIRE THROUGH A SHEATH │
│              LUMEN EXTENDING A SHEATH                       │
└─────────────────────────────────────────────────────────────┘
                              ⬇
┌─────────────────────────────────────────────────────────────┐
│ Step 362: MOVING THE SHEATH DISTALLY ALONG THE GUIDEWIRE UNTIL A │
│ DISTAL END OF THE SHEATH IS ENGAGED WITH THE SHEATH GUIDE BODY   │
│ AND AN EXTERIOR DIAMETER OF THE SHEATH IS COAXIAL WITH THE       │
│                        CENTRAL AXIS                              │
└─────────────────────────────────────────────────────────────┘
                              ⬇
┌─────────────────────────────────────────────────────────────┐
│ Step 364: REMOVING THE GUIDEWIRE FROM THE CAVITY THROUGH THE │
│                       SHEATH LUMEN                           │
└─────────────────────────────────────────────────────────────┘

*FIG. 4D*

ACCESS DEVICES AND ASSOCIATED METHODS

CROSS-REFERENCE TO RELATED APPLICATIONS

This patent application claims the benefit of priority under 35 U.S.C.§ 119 to U.S. Provisional Patent Application No. 62/402,555, filed Sep. 30, 2016, which is herein incorporated by reference in its entirety.

TECHNICAL FIELD

Aspects of the present disclosure generally relate to medical devices and procedures. In particular, aspects of this disclosure relate to access devices and associated methods.

BACKGROUND

Percutaneous nephrolithotomy ("PCNL") is a reliable approach for managing kidney stones. Similar approaches may be used to remove a kidney stone positioned in a body where other (e.g., ureteroscopic) approaches would be less effective. For example, PCNL may be the preferred for treating: staghorn calculi or large (e.g., greater than 2 cm) intrarenal stones; stones with concomitant ureteropelvic junction obstruction; and/or intrarenal stones not amenable to extracorporeal shockwave lithotripsy ("SWL") or endoscopic management due to stone composition or anatomic variability.

In some PCNL procedures, a needle is inserted through the body and into a kidney for management of the kidney stones. Optimal kidney access is necessary for ensuring a successful and complication-free PCNL procedure. Known methods for gaining access may be time-consuming and/or introduce other complications. For example, a surgeon may be required to use and re-position an X-ray device about the patient numerous times define an access tunnel. These efforts may consume operating time and expose the patient to higher amounts of radiation.

Maintaining the access tunnel can also be a problem. In some procedures, an adjustable jig-like device is used to maintain the tunnel by manipulation of various mechanical components, such as gears and the like. These devices may be mechanically complex, requiring the surgeon to familiarize herself with mechanics of a particular device, and/or manipulate that device during a PCNL procedure, both time consuming tasks. Moreover, these devices typically cannot be modified to accommodate the unique shape and size of a particular patient, or the unique demands of a particular PCNL procedure.

Further improvements are required. Accordingly, the access devices and methods described herein are provided to rectify deficiencies described in the prior art and offer improvements that address other known problems specific thereto.

SUMMARY

Aspects of the present disclosure relate to access devices and associated methods. Numerous aspects of the present disclosure are now described.

One aspect of this disclosure is a device. The device may be an access device configured to guide an elongated element (e.g., a needle) through a body tissue (e.g., skin). For example, the device may comprise: a needle guide body extending along a central axis between a distal end and a proximal end, a needle guide lumen extending through the distal and proximal ends of the needle guide body along the central axis, and a base monolithically attached to the needle guide body to define a non-variable patient-specific insertion path.

In some aspects, the needle guide body may be removably attached to the base. For example, the needle guide body may be removably attached to the base by one or more frangible portions. A proximal end of the needle guide body may be offset from the base along the central axis by a patient-specific depth. The proximal end of the needle guide body may be configured to guide a tip of a needle into the needle guide lumen. A distal surface of the base may include patient-specific contouring, and/or perimeter of the base may include one or more elements configured to retain a portion of a guidewire.

In other aspects, the device may further comprise: a sheath guide body extending along the central axis between a distal end and a proximal end; and a sheath guide lumen extending through the distal and proximal ends of the sheath guide body along the central axis, wherein the needle guide lumen is contained with the sheath guide lumen, and the distal end of the sheath guide body is attached to the base. The needle guide body may be removably attached to the base, and the sheath guide body may be divided into a plurality of sheath guide walls arranged about the central axis. The sheath guide body also may be engageable with a distal end of a sheath so that an exterior diameter of the sheath is coaxial with the central axis.

Another aspect of this disclosure is a method of using an access device. An exemplary method according to this aspect may comprise: positioning a base of a device against a tissue, the device including a needle guide body extending along a central axis between a distal end and a proximal end, and a needle guide lumen extending through the distal and proximal ends of the needle guide body along the central axis, wherein the needle guide body is attached to the base; attaching the base to the tissue so as to maintain alignment of the central axis with a patient-specific insertion path through the tissue; and moving a needle distally through the needle guide lumen in order to penetrate the tissue along the patient-specific insertion path.

According to this aspect, the method may further comprise moving the needle distally through the needle guide lumen by a patient-specific depth. The needle may have a needle lumen extending therethrough, and the method may further comprise: moving a guidewire distally through the needle until at least a distal end of the guidewire is located in the cavity; and moving the needle proximally along the guidewire without removing the distal end of the guidewire from the cavity. The needle guide body may be removably attached to the base, and the method may further comprise: removing the needle from the body; and detaching the needle guide body from the base without removing the distal end of the guidewire from the cavity.

As a further example, the device may further include a sheath guide body extending along the central axis between a distal end and a proximal end, and a sheath guide lumen extending through the distal and proximal ends of the sheath guide body along the central axis, wherein the needle guide lumen is contained with the sheath guide lumen, and the distal end of the sheath guide body is attached to the base. In which case, this method may further comprise: threading a proximal end of the guidewire through a sheath lumen extending through a sheath; moving the sheath distally along the guide wire until a distal end of the sheath is engaged with the sheath guide lumen and an exterior diameter of the sheath is coaxial with the central axis; and removing the guidewire from the body through the sheath lumen.

Yet another aspect of this disclosure is a method of producing and/or using an access device. An exemplary method may comprise: creating a patient-specific data set including an insertion point on the tissue, an insertion path between the insertion point and the cavity, and an insertion depth between the insertion point and the cavity along the path; and producing a device from the data set, the device including: a needle guide body extending along a central axis between a distal end and a proximal end, a needle guide lumen extending through the distal and proximal ends of the needle guide body along the central axis, and a base monolithically attached to the needle guide body to define a non-variable patient-specific insertion path.

According to this aspect, the patient-specific data set may include one or more dimensions of a sheath, and the device may be produced to include: a sheath guide body extending along the central axis between a distal end and a proximal end, and a sheath guide lumen extending through the distal and proximal ends of the sheath guide body along the central axis, wherein the sheath guide lumen is sized approximate to the one or more dimensions of the sheath, the needle guide lumen is contained with the sheath guide lumen, and the distal end of the sheath guide body is attached to the base. In some aspects, the patient-specific data may include a topography of a surface contour on the tissue at the insertion point, and the device may be produced to include a patient-specific contouring that corresponds with the topography. The patient-specific data may include one or more dimensions of a needle, and the device may be produced to include a needle stop surface offset from the base by a distance approximate to the one or more dimensions of the needle.

Producing the device according to these aspects may comprise communicating the data set to a 3D printer and printing the device with a 3D printer. Accordingly, some methods may further comprise: positioning the base of the device against a tissue; attaching the base to the tissue to maintain alignment of the central axis with the patient-specific insertion path; and moving a needle distally through the needle guide lumen in order to penetrate the tissue along the patient-specific insertion path. Any method described herein may be performed subsequent to printing.

It may be understood that both the foregoing summary and the following detailed descriptions are exemplary and explanatory only, neither being restrictive of the inventions claimed below.

BRIEF DESCRIPTION OF THE DRAWINGS

The accompanying drawings are incorporated in and constitute a part of this specification. These drawings illustrate aspects of the present disclosure that, together with the detailed written descriptions provided herein, serve to explain the principles of this disclosure.

FIGS. 4A-D depict another exemplary method according to this disclosure.

DETAILED DESCRIPTION

Aspects of the present disclosure are now described with reference to exemplary devices and methods. Some aspects are described with reference to a PCNL procedure, wherein a needle is guided into a kidney with a needle guide to manage a kidney stone. Various needle guides are described. Each needle guide may be produced during the PCNL procedure according to a patient-specific data set collected at any point (e.g., during the procedure) using the methods described herein. References to a particular procedure, such as PCNL; material, such as a kidney stone; cavity, such as the interior of a kidney; or time, such as during a procedure, is provided for convenience and not intended to limit the present disclosure unless claimed. Accordingly, the concepts described herein may be utilized for any analogous device or method—medical or otherwise.

Figure 1:
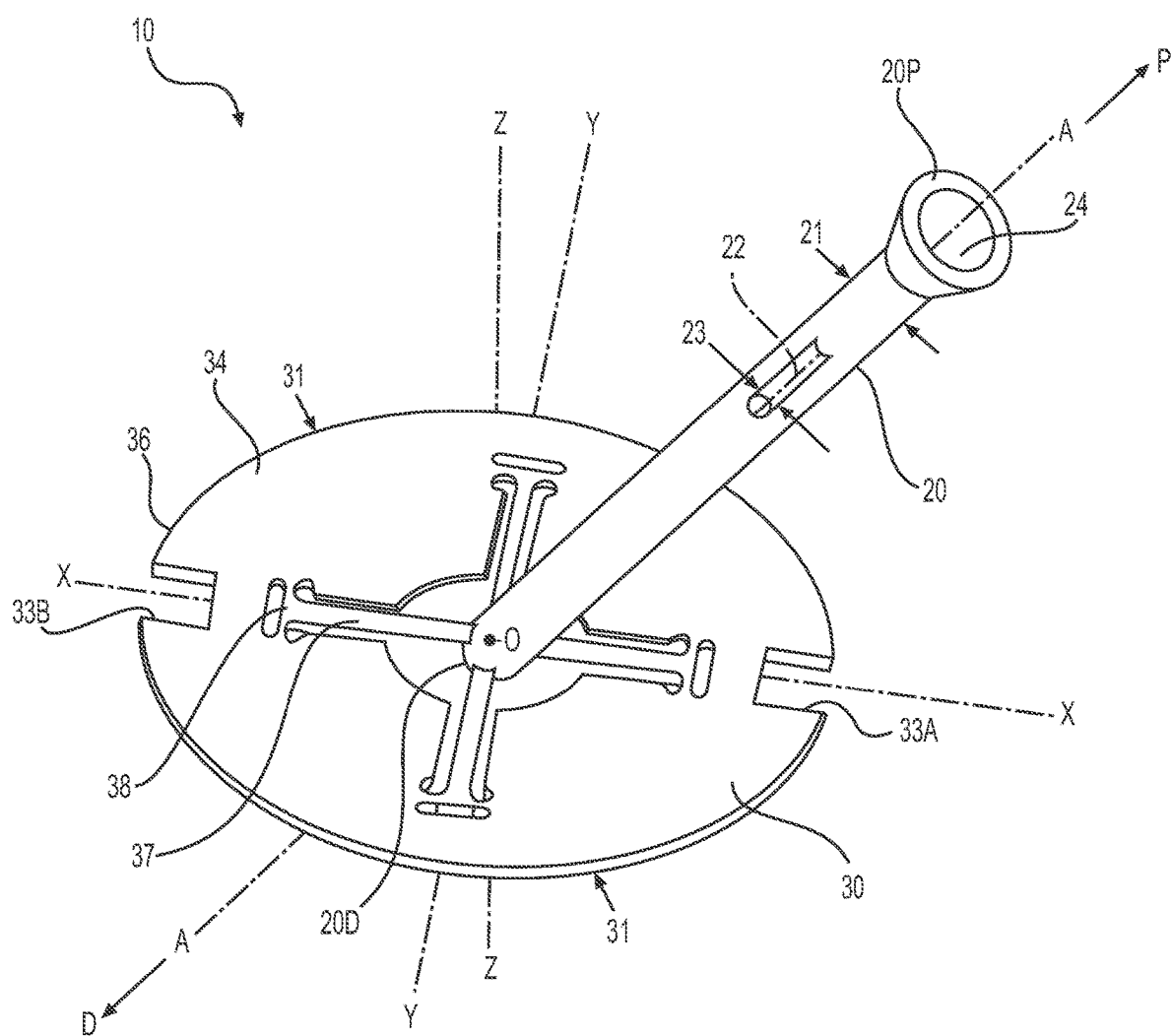
FIG. 1 depicts a perspective view of an exemplary device according to this disclosure.

Numerous axes are described. In particular, a set of three directional axes, including an X-X axis, Y-Y axis, and Z-Z axis, are described with reference to an origin point O (FIG. 1). Each axes may be transverse, or even perpendicular, with the next so as to establish a Cartesian coordinate system. The directional terms "proximal" and "distal," and their respective initials "P" and "D," may be similarly used to describe relative components and features. Proximal refers to a position closer to the exterior of the body or a user, whereas distal refers to a position closer to the interior of the body or further away from the user. Appending the initials "P" or "D" to an element number signifies a proximal or distal location, and appending P or D to an arrow in a figure signifies a proximal or distal direction. Unless claimed, these terms are provided for convenience and not intended to limit the present disclosure to a particular location, direction, or orientation.

As used herein, the terms "comprises," "comprising," or like variation, are intended to cover a non-exclusive inclusion, such that a device or method that comprises a list of elements does not include only those elements, but may include other elements not expressly listed or inherent thereto. Unless stated otherwise, the term "exemplary" is used in the sense of "example" rather than "ideal." Conversely, the terms "consists of" and "consisting of" are intended to cover an exclusive inclusion, such that a device or method that consists of a list of elements includes only those elements.

Aspects of the present disclosure pertain to an exemplary device 10. According to one aspect, illustrated for example in FIG. 1, device 10 may comprise a needle guide body 20 extending along a needle guide body central axis A-A, a needle guide lumen 22 extending through body 20 along axis A-A, and a base 30 attached to the needle guide body 20. In FIG. 1, these elements may be defined with respect to a set of axes X-X, Y-Y, and Z-Z that form a coordinate system about an origin point O located, in this example, at a central point of base 30. Within this coordinate system, central axis A-A may be geometrically defined as a vector passing through origin point O within a plane defined by axes X-X and Z-Z. Any movements along central axis A-A may be defined as proximal or distal in a proximal-distal direction along axis A-A, as indicated by the respective P and D arrows shown in FIG. 1.

In FIG. 1, needle guide body 20 is depicted as a cylindrical element having an exterior diameter 21 coaxial with central axis A-A, although any geometric shape may be used, cylindrical or otherwise. Needle guide body 20 extends between a distal end 20D and a proximal end 20P along axis A-A. Distal end 20D is attached to base 30. Proximal end 20P may be configured to guide a tip of a needle into needle guide lumen 22. For example, as shown in FIG. 1, proximal end 20P may define a funnel 24 with an interior surface sloped into lumen 22 from a first diameter larger than an inner diameter 23 of lumen 22, to a second diameter equal to diameter 23. The proximal-facing surface of proximal end 20P may define a needle stop (e.g., a ledge, protrusion, or like shape) engageable with the needle (or a corresponding structure on the needle) to limit its movement in the proximal-distal direction along axis A-A.

Needle guide lumen 22 is depicted in FIG. 1 as a cylindrical bore. Interior diameter 23 shown as coaxial with axis A-A, although any geometric shape and/or axial arrangement may be used. Lumen 22 extends through an opening located at each of the respective distal and proximal ends 20D and 20P of needle guide body 20, and is sized to receive a needle therethrough. In some aspects, for example, the interior diameter 23 of lumen 22 is approximate to or larger than an exterior diameter (or gauge) of the needle to ensure that the needle (e.g., an 18 gauge hypodermic needle) may be passed through lumen 22 along central axis A-A. Although depicted in FIG. 1 as including a single lumen 22, body 20 may be modified to include a plurality of lumens 22, at least (or only) one of which is coaxial with axis A-A and/or sized to receive a needle. For example, device 10 may consist of a single needle guide lumen 22, as shown in FIG. 1.

The exemplary base 30 of FIG. 1 is depicted as a substantially planar element having an exterior diameter 31 coaxial with axis A-A, a proximal or top surface 34, and a distal or bottom surface 36. In this example, origin point O is located on distal surface 36, at the center of exterior diameter 31. Base 30 may be attached to a tissue so that distal surface 36 is pinned against the tissue, positioning origin point O firmly at the interface between surface 36 and a patient-specific entry point on the tissue. For example, base 30 may be attached to the tissue so that an X-Y plane defined by distal surface 36 accords with a corresponding X-Y plane defined by the tissue. In some aspects, the surface area base 30 is small (e.g., less than 1 square inch) so that distal surface 36 may be substantially planar even if intended for placement against a curved portion of tissue. In other aspects, the tissue may have a patient-specific topography (e.g., bumps, curves, etc.), and distal surface 36 may include patient-specific contouring that corresponds with the patient-specific topography. An adhesive (e.g., glue) and/or an adhesive element (e.g., tape) may attach base 30 to the tissue. For example, distal surface 36 may be coated with adhesive and/or attached to another adhesive element (e.g., double-sided medical tape). Non-adhesive elements (e.g., sutures) may also be employed.

Base 30 is attached to distal end 20D of needle guide body 20 so as to maintain alignment of central axis A-A with a patient-specific insertion path through a tissue when base 30 is attached to the tissue. The patient-specific insertion path may extend between an insertion point on the tissue (e.g., a point on the skin located approximate to a kidney) and a cavity located distal of the tissue (e.g., an interior portion of the kidney, such as a calyx). Accordingly, central axis A-A of device 10 may be aligned with this insertion point to permit insertion of a needle through the tissue along the patient-specific insertion path. Base 30 and distal end 20D of needle guide body 20 are attached so as to maintain this alignment when base 30 is attached to the tissue. For example, in some aspects, distal end 20D may be formed integral with, rigidly attached, or otherwise monolithically coupled to base 30 so as to provide a rigid, stable, non-variable connection between end 20D and base 30.

In some aspects, distal end 20D of needle guide body 20 may be removably attached to base 30. For example, as depicted in FIG. 1, distal end 20D is attached to base 30 by a plurality of legs 37 (e.g., four) spanning therebetween. In FIG. 1, for example, each leg 37 extends along one of axes X-X or Y-Y between needle guide body 20 and an interior portion of base 30 to stabilize needle guide body 20. Each leg 37 also may be attached to base 30 by a frangible portion 38 configured to break in response to a removal force applied to guide body 20, such as a twisting force applied to body 20 about central axis A-A. As shown in FIG. 1, each frangible portion 38 includes a cross-bar spanning between the sidewalls of an opening formed in base 30. Each leg 37 is attached to one of the crossbars such that application of a twisting force will shear the crossbars away from base 30, allowing body 20 to be removed.

Aspects of base 30 may be further configured for use in a PCNL procedure. For example, base 30 of FIG. 1 further includes a pair of notches 33A and 33B formed into exterior diameter 31 in FIG. 1. Notches 33A and 33B are aligned with axis X-X and, as such, may be used to align base 30 with, for example, a line drawn between a first point A and second point B drawn on the tissue to signify a direction of a patient-specific insertion path, as described below with reference to FIGS. 3A-C. In some aspects, notches 33A and 33B may be configured to retain an elongated device (e.g., a guidewire) adjacent base 30 (e.g., by pinning the device to base 30), or engage base 30 with another medical device (e.g., a platform attached to the body). Numerous other support elements may extend away from or be attached a portion of base 30, including hooked elements that secure a sterile drape to base 30, and/or protrusions that support attachment of another device to base 30 (e.g., a light source).

Other aspects of the present disclosure pertain to a device 110 that includes some counterpart elements of device 10, but within the 100 series of numbers. For example, similar to device 10 of FIG. 1, device 110 of FIG. 2 includes a needle guide body 120 extending along a central axis A-A, and a needle guide lumen 122 extending therethrough. Central axis A-A of FIG. 2, like axis A-A of FIG. 1, may be geometrically defined as a vector passing through origin point O. In contrast to device 10, device 110 further includes a sheath guide body 140 extending along central axis A-A, and a sheath guide lumen 142 extending through body 140.

Figure 2:
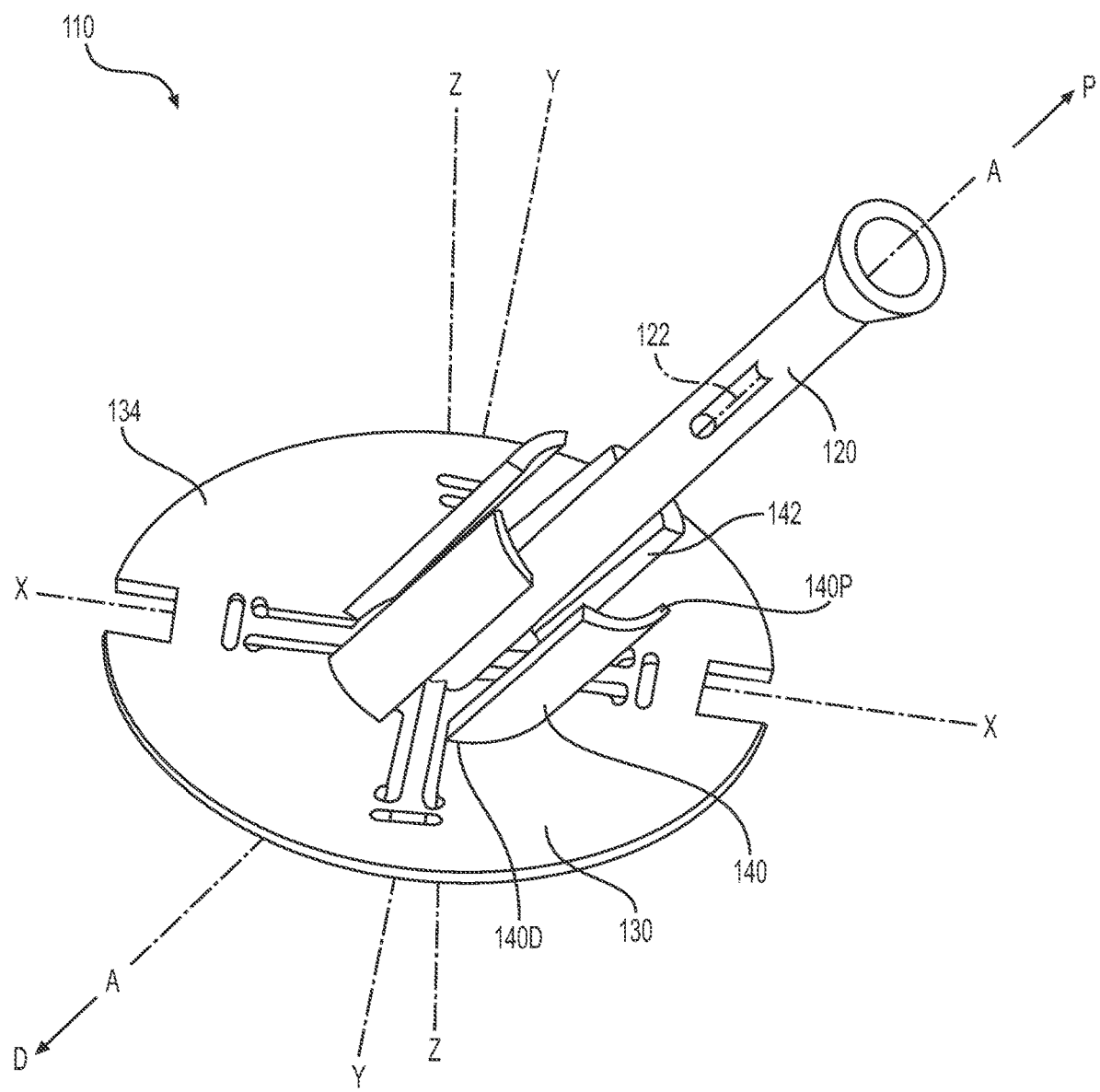
FIG. 2 depicts a perspective view of another exemplary device according to this disclosure.

In FIG. 2, sheath guide body 140 is depicted as a cylindrical element having an exterior diameter coaxial with central axis A-A, although any geometric shape may be used. Sheath guide body 140 may, as shown, include an annular wall extending along axis A-A between a distal end 140D and a proximal end 140P. Sheath guide lumen 142 is depicted as a cylindrical bore having an interior diameter extending along axis A-A through an opening located at each of the respective proximal and distal ends 140D and 140P of the cylindrical sheath guide body 140. As shown in FIG. 2, needle guide body 120 is contained within sheath lumen 142 so that a sheath (e.g., an elongated tube) may be advanced over needle guide body 120.

Sheath guide body 140 may be engageable with the sheath so that an interior diameter of the sheath is coaxial with central axis A-A. For example, the sheath may include a sheath lumen with an interior diameter greater than the exterior diameter of guide body 140, in which case the sheath is fit over sheath guide body 140; or the sheath may have an external diameter that is less than the interior diameter of guide lumen 142, in which case the sheath is fit into sheath guide lumen 142. Either way, when a distal end of the sheath is attached to guide body 140 (e.g., frictionally engaged), then the sheath and/or sheath lumen may be coaxial with axis A-A so that an elongated device (e.g., an optical fiber) may be advanced through the sheath lumen. For example, the elongated device may be moved through the sheath lumen in a proximal-distal direction along central axis A-A until a distal end of the elongated device is moved adjacent a proximal surface 134 of base 130 for contact with a tissue.

As shown in FIG. 2, sheath guide body 140 may include an annular wall defined by a plurality of (e.g., four) wall potions. Each wall portion is arranged about axis A-A in FIG. 2 to stabilize and guide the sheath. These wall portions may be further configured for engagement with a distal portion of the sheath. For example, each wall portion depicted in FIG. 2 may be configured to flex relative to axis A-A, as needed, to engage the a distal portion of the sheath located adjacent a distal-most end of the sheath. For example, the plurality of wall portions may be sized and configured to achieve a friction fit with an exterior surface located at the distal portion of the sheath, and/or include an attachment element (e.g., a set of threads) engageable with a corresponding structure on the sheath (e.g., another set of threads). A locking mechanism (e.g., adhesive or mechanical) may also be provided to lock the distal end of the sheath together with sheath guide body 140.

Another aspect of the present disclosure is a method 300 of using device 10, device 110, or a variation thereof. Method 300, as depicted in FIG. 3 for example, is described with reference to device 10, which includes needle guide body 20 extending along central axis A-A between distal and proximal end 20D, 20P, and needle guide lumen 22 extending through body 20 along axis A-A, with distal end 20D being attached to base 30 as described above. Accordingly, aspects of method 300 may comprise: positioning base 30 against a tissue (310); attaching base 30 to the tissue so as to maintain alignment of the central axis with a patient-specific insertion path through the tissue (320); and moving a needle distally through needle guide lumen 22 to penetrate the tissue along the patient-specific insertion path (330). Numerous additional and/or intermediate aspects of method 300 may be configured to leverage the unique structural features of device 10, 110, or the like, as now described.

Method 300 may include a number of preceding steps, such as locating the patient internal cavity, and determining the patient-specific path. These steps are described further below with respect to a method 400. In some aspects, method 300 at 330 may further include moving the needle distally through needle guide lumen 22 by a patient-specific depth along axis A-A. For example, as noted above, a proximal-facing surface of proximal end 20P, such as the proximal-most surface or a ledge extending away from body 20, may define a needle stop engageable with the needle to limit its movement along axis A-A. Accordingly, if a length of needle guide body 20 along axis A-A between distal and proximal ends 20D and 20P is equal to an insertion depth along the patient-specific path, then the needle may achieve that insertion depth when moved distally in lumen 22 until, for example, a distal facing surface of the needle contacts a portion of proximal end 20P.

Aspects of method 300 may be configured for use in a particular medical procedure, such as PCNL procedure. For example, the needle may have a needle lumen extending therethrough to receive an elongated element, such as a guidewire. Thus, method 300 may further comprise moving the guidewire distally through the needle until at least a distal end of the guidewire is located in the cavity (340). At this point, the guidewire now extends along the patient-specific insertion path between device 10 and an interior portion of the cavity. Thus, method 300 may further comprise moving the needle proximally along the guidewire without removing the distal end of the guidewire from the cavity (342). For example, the needle may be moved proximally along the guide wire until removed from body.

As described above, the distal end 20D of needle guide body 20 may be removably attached to base 30, as depicted in FIG. 1. Therefore, method 300 may further comprise: removing the needle from the cavity along the guidewire (350); and/or removing the needle guide body 20 from the base 30 along the guidewire (352). For example, method 300 at 350 may include applying a removal (e.g., rotational) force to needle guide body 20 that permits removal of the distal end 20D of guide body 20 from base 30 (e.g., by breaking all of frangible portions 38). Alternatively, portions 38 might be cut with a scalpel, or with a distal edge of a cylindrical cutting tool, with any other surgical tool engageable with portions 38. Guide body 20, once broken free from base 30, may be moved proximally along the guide wire, together with or independent of the needle, and without moving the distal end of the guidewire out of the cavity. Other medical devices may then be moved into the cavity along the guidewire, and thus along the patient-specific path, without interference from needle guide body 20.

Aspects of method 300 may be modified for use with device 110, which, in addition to the counterpart elements of device 10 described above, may include: sheath guide body 140 extending along central axis A-A between distal and proximal ends 140D and 140P, and sheath guide lumen 142 extending through body 140 along the axis A-A, wherein needle guide body 120 is contained within sheath guide lumen 142, and distal end 140D of sheath guide body 140 is attached to a base 130. Accordingly, after needle guide body 120 has been removed from base 130 at 352, for example, method 300 may further comprise: moving a proximal end of a guidewire through a sheath lumen extending through a sheath (360); moving the sheath distally along the guide wire until a distal end of the sheath is engaged with the sheath guide body 140 and an exterior diameter of the sheath is coaxial with central axis (362); and removing the guidewire from the body through the sheath lumen (364). Because the exterior diameter of the sheath is coaxial with axis A-A, and needle guide body 120 has been removed, method 300 may further comprise moving an elongated device (e.g., an optical fiber) into the cavity along the patient-specific insertion path through the sheath lumen, or other lumen extending through the sheath.

Figure 4A:
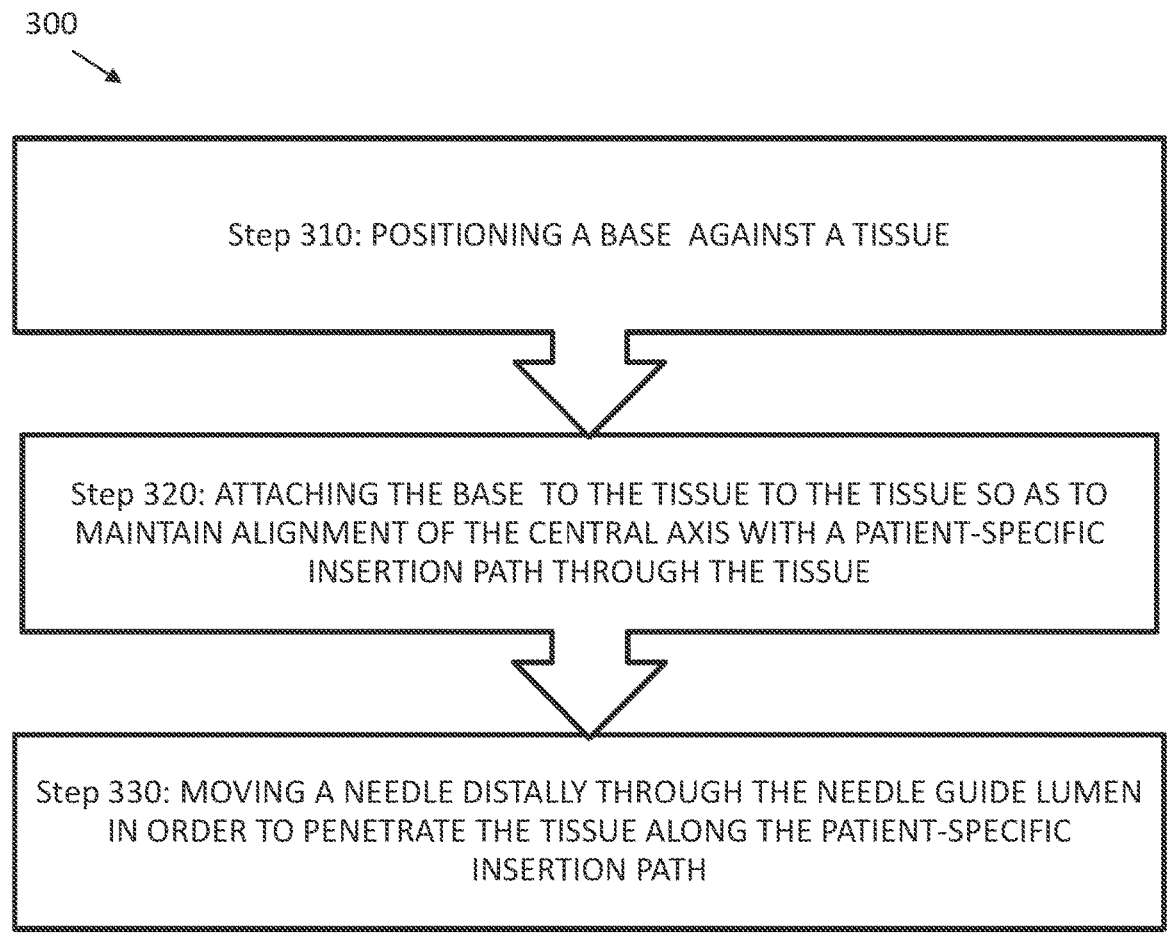
Figure 4B:
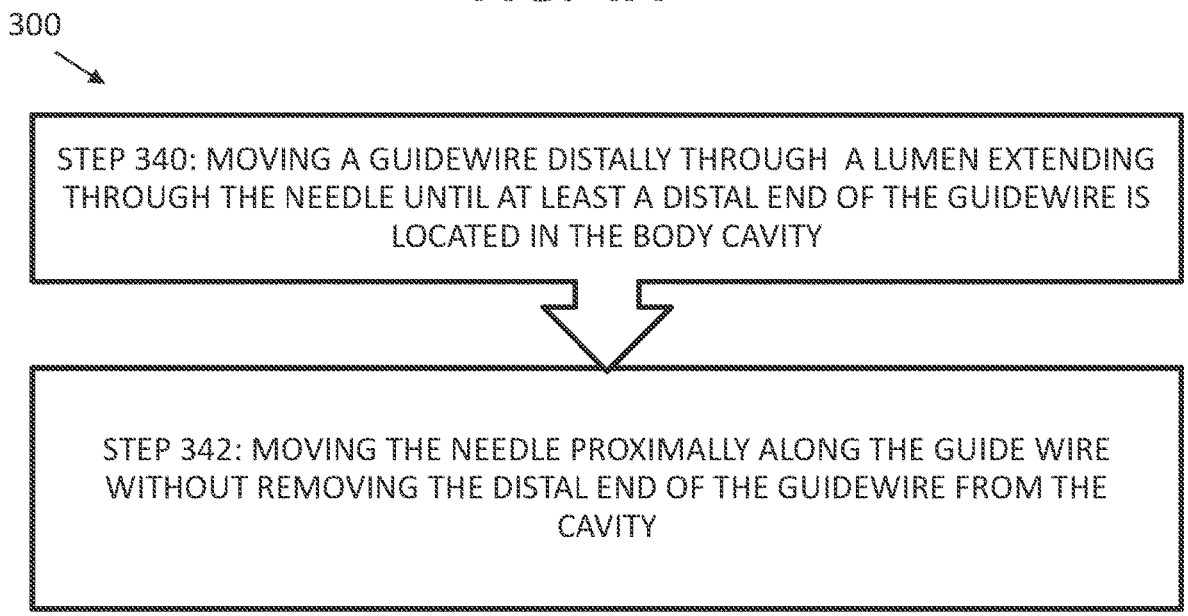

Yet another aspect of the present disclosure is a method 400 of production and/or use. As described above, various aspects of device 10 may be patient-specific, meaning that the geometric parameters of these aspects are determined in response to a patient-specific data set. Method 400 may be used to create the patient-specific data set, and use the data set to produce device 10. For example, as shown in FIG. 4, method 400 may comprise: locating a cavity disposed distal of a tissue (410); creating a patient-specific data set including an insertion point on the tissue, an insertion path between the insertion point and the cavity, and an insertion depth between the insertion point and the cavity along the insertion path (420); and producing device 10 from the patient-specific data set (430).

The cavity may be located at 410 using any known method, including those involving a visualization device, such as an X-ray device or fluoroscope. Such methods may be performed using a diluted contrast instilled into a cavity. For example, in a PCNL procedure, the diluted contrast may be instilled into a kidney via a preplaced ureteric catheter to add opacity to the kidney and other collection systems in communication therewith. Once the cavity has been located, method 400 at 420 may be used to create the patient-specific data set.

Figure 3C:
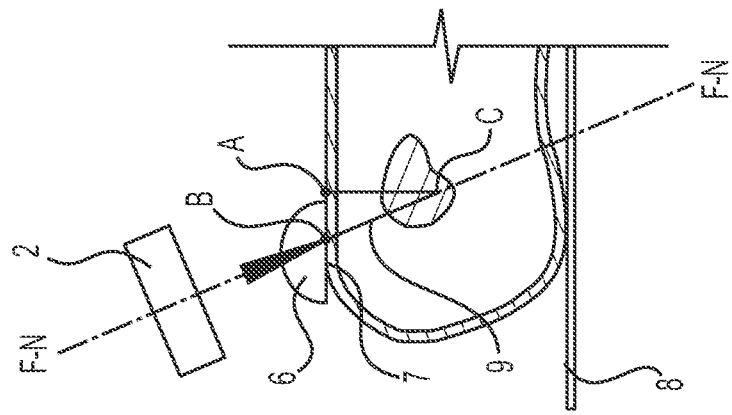
FIGS. 3A-C depict an exemplary method according to this disclosure.
Figure 3B:
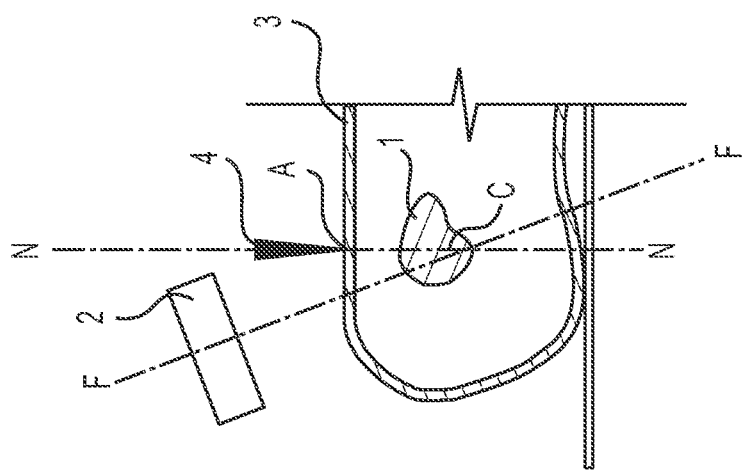
Figure 3A:
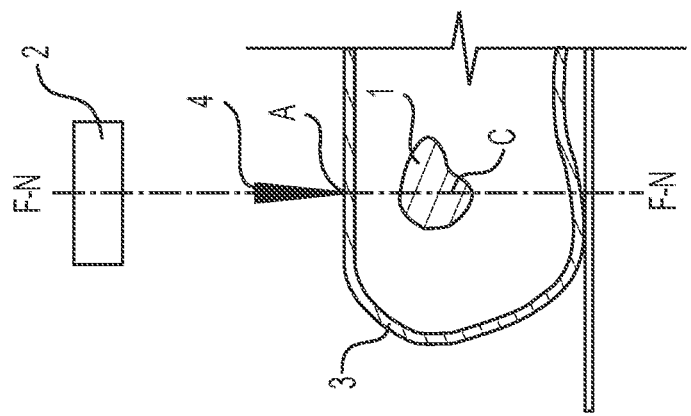

In some aspects, method 400 at 420 may comprise creating the patient-specific data set using a bull's eye technique or a triangulation technique. A PCNL specific example of the bull's eye technique is depicted in FIGS. 3A-C, wherein the insertion angle and depth are determined by locating series of points on the tissue. As shown in FIG. 3A, for example, a fluoroscope 2 having a trajectory F-F may be placed over a kidney 1 so that trajectory F-F of fluoroscope 2 extends through a targeted point C inside of kidney 1, which may be located in a particular calyx. A longitudinal axis N-N of needle 4 may be aligned with trajectory F-F (indicated by the combined axis F-N depicted in FIG. 3A) to achieve the bull's eye effect. After which, a tip of needle 4 is used to mark a first position A located at a portion of skin 3 overlying targeted point C of kidney 1 along trajectory F-F.

In FIG. 3B, fluoroscope 2 has been rotated (e.g., by about 30° toward the surgeon) about targeted point C. Needle 4 is the moved about skin 3 to arrive at a second position B (FIG. 3C), wherein the longitudinal axis N-N is once again aligned with trajectory F-F (forming combined axis F-N) to achieve the bull's eye effect. The tip of needle 4 is again used to mark second position B. A marking element may then be used to draw a line AB between first and second positions A and B. This line may, as noted above, be aligned with notches 33A and 33B to position device 10. With second point B marked, the insertion angle may be determined by placing a protractor 6 adjacent the skin, aligning a bottom surface 7 of protractor 6 with line AB and a top surface of an operating table 8, and measuring the angle between combined axis F-N and bottom surface 7. As shown in FIG. 3C, a hypothetical right triangle 9 may be formed between points A, B, and C, thereby allowing the penetration depth between points B and C to be calculated from the insertion angle in combination with the measured distances between points A and B, and A and C. With slight modification, a skilled artisan would recognize that the triangulation technique may be similarly applied.

Method 400 at 420 may alternatively comprise using an automated method to create the patient-specific data set. For example, the insertion point, angle, and depth may be determined without protractor 6 using computer-aided methods for scanning a body with visualization device, and analyzing the output of the visualization device with a processor. For example, these variables may be determined from a three-dimensional scan of the body without need for making physical contact with skin 3. However the patient-specific data set is defined, method 400 at 420 may further comprise sending the data set to one or more processor for further analysis, and/or converting the data set into a format usable with a production device. Other computer-aided devices and methods are described below with reference to device 500.

Method 400 at 430 comprises producing device 10 from the patient-specific data set (430). For example, consistent with above, device 10 may be produced to include a needle guide body 20, a needle guide lumen 22 extending therethrough, and a base 30 attached to guide body 20. Numerous means of production are contemplated. For example, producing device 10 may comprise communicating the patient-specific data set to a 3D printer; and printing the device, with the 3D printer, from the data set. In this example, method 400 at 420 may, for example, further comprise converting the data set into a format useable by the 3D printer, such as STL, VMRL, and the like.

In some aspects, the patient-specific data set may be obtained prior to surgery so that device 10 may be produced in advance. For example, the data set may be sent to a remote production facility, and then delivered to the operating room prior to surgery. Alternatively, given the production speed of some 3D printers, device 10 may be alternatively produced at a point proximate to the surgery (e.g., during the surgery). Aspects of method 400 may, thus, be combined with aspects of method 300 in a single procedure. For example, all or any portion of method 300 may be performed after device 10 has been produced (e.g., printed). Method 400 may likewise be modified for use with device 110. For example, device 110, consistent with above, may be printed from the patient-specific data set to include a sheath guide body 140, and a sheath guide lumen 142 extending therethrough.

Still other aspects of device 10 or 110 may be produced in a patient-specific manner. For example, method 400 at 420 may further comprise determining a patient-specific topography of a surface contour on the tissue at second point B by scanning the tissue with a visualization device. By including this topography in the patient-specific data set, distal surface 34 of base 30, for example, may be produced to include a patient-specific contouring that corresponds with (e.g., interlocks) with the topography to further stabilize device 10 on the tissue. Numerous other aspects of devices 10 and 110 may likewise be produced to include patient-specific features. For example, the patient-specific data set may include additional variables so that needle guide lumen 22 may be sized according to the exterior dimension of a particular needle, and/or sheath guide lumen 42 may be sized for engagement with a particular sheath. The materials used to produce devices 10 and 110 may also be patient-specific. For example, device 10 may be produced from a printable polymer uniquely biocompatible with a particular patient.

It should also be appreciated that method 400 may alternatively be used with any medical device, including devices 10 and 110, and any similar devices having a similar configuration. For example, method 400 may likewise be used to produce, from a patient-specific data set, any medical device intended for placement against an external tissue (e.g., skin) or implantation against an internal tissue (e.g., a bladder).

Figure 6:
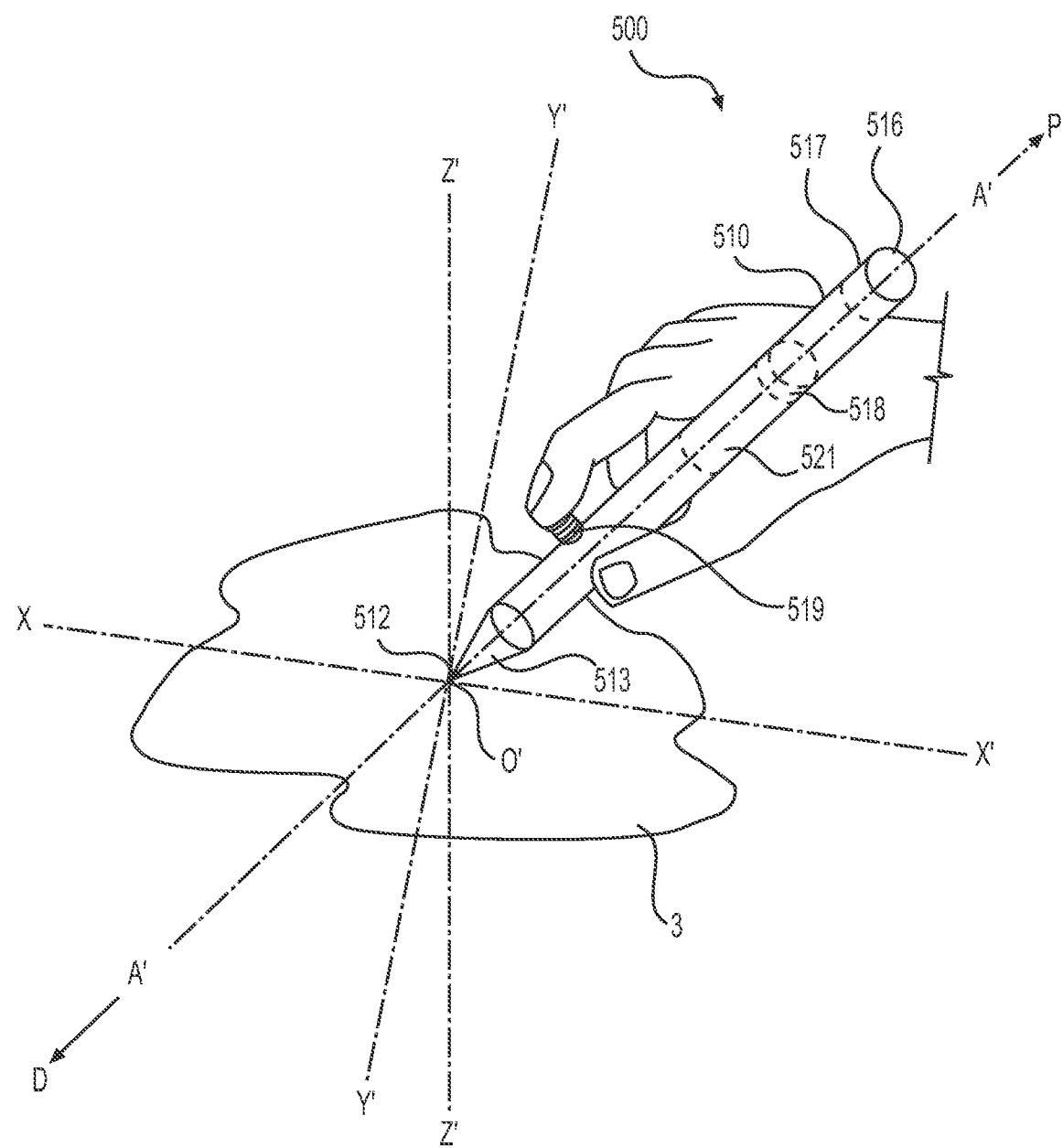
FIG. 6 depicts a perspective view of an exemplary measurement device according to this disclosure.

Yet another aspect of the present disclosure is a measurement device configured to generate a patient-specific data set usable within method 400 to produce device 10, device 110, and the like. An exemplary measurement device 500 is depicted in FIG. 6 as an elongated, pen-like object. Measurement device 500 may be used like needle 4 to generate the patient-specific data set by automatically capturing the geometric data associated with a plurality of positions of device 500 relative to origin point O'. For example, device 500 may be pivoted about origin point O' to establish the patient-specific data set using either the bull's eye technique or the triangulation technique (e.g., as depicted in FIGS. 3A-C) by automatically or manually recording the geometrical relationship of device 500 relative to skin 3.

According to one aspect, as shown in FIG. 6, measurement device 500 may comprise an elongated body 510 extending along a longitudinal axis A'-A' between a distal or contact point 512 and a proximal end 516. Body 510 may be grasped by a hand, much like needle 4. Contact point 512 may, in some aspects, be configured to physically engage a tissue (e.g., a portion of skin 3) and establish a pivot or origin point O' for device 500. Device 500 may include one or more positional sensors for determining, in real-time, the position of longitudinal axis A'-A' (and thus device 500) relative to origin point O'. For example, device 500 of FIG. 6 has a first sensor bay 513 at contact point 512 and a second sensor bay 517 distal of proximal end 516. Bays 513 and 517 may each include a plurality of ultrasound transducers configured to determine distances between body 510 and the tissue. When contact point 512 is engaged with an exemplary portion of skin 3, and body 510 is pivoted, first sensor bay 513 may remain in a fixed position relative to second sensor bay 517, allowing for determination, with one of the ultrasound transducers, a distance between second sensor bay 517 and skin 3 in at least one plane. A plurality of similar distances can be determined in other planes and integrated to geometrically define aspects of the patient-specific data set, such as the position of axis A'-A' relative to origin point O'.

According to one aspect, device 500 includes a controller 518 operable to automatically or manually establish origin point O' and other aspects of the patient-specific data set. For example, device 510 of FIG. 6 includes a switch 519 operable with controller 518 to establish origin point O' when a user activates switch 519. Alternatively, first sensor bay 513 may include a pressure sensor operable with controller 518 to establish origin point O' when contact point 512 is placed against skin 3. Controller 518 may assume the position of each axes X'-X', Y'-Y', and Z'-Z' in the data set, for example, as a Cartesian coordinate system centered on point O'. Other aspects of the patient specific data set may then be determined with this system. For example, as shown in FIGS. 2 and 6, if body 510 is pivoted about origin point O' using the bull's eye technique, then switch 519 may be activated each time body 510 is aligned with trajectory F-F to geometrically define a plurality of data points on the assumed Cartesian system. In FIG. 6, these data points may be sent by a transmitter 521 to one or more processors configured to determine, for example, the patient specific insertion path therefrom.

Aspects of method 400 may be modified to incorporate measurement device 500. Any aspect of method 400 described herein may be modified according to the functional and structural features of device 500 described above. For example, as described above, method 400 at 420 may be performed with device 500 responsive to controller 518 and/or switch 519.

Even a slight deviation in the insertion angle or depth can direct a needle off course and/or into undesired locations. This risk can be reduced by ensuring that device 10 is accurately produced. Therefore, a further aspect of the present disclosure is a verification device 600 configured to determine whether device 10 has been actually been produced according to a patient-specific data set. An exemplary device 600 may include a housing 620, an interior bay 622 of housing 620, and one or more scanners configured to output geometric data. Any scanning technology may be used. For example, in FIG. 7, interior bay 622 includes a first ultrasound transducer 610A aligned with an axis X"-X" extending through an origin point O", a second ultrasound transducer 610B aligned with an axis Y"-Y" extending through point O", and a third ultrasound transducer 610C aligned with an axis Z"-Z" extending through origin point O". Accordingly, when device 10 is placed in bay 622, transducers 610A-C may be configured to scan the physical shape of device 10 along each axes X"-X", Y"-Y", and Z"-Z"; and output geometric data (e.g., physical measurements) of device 10 relative to those axes and original point O".

Figure 5A:
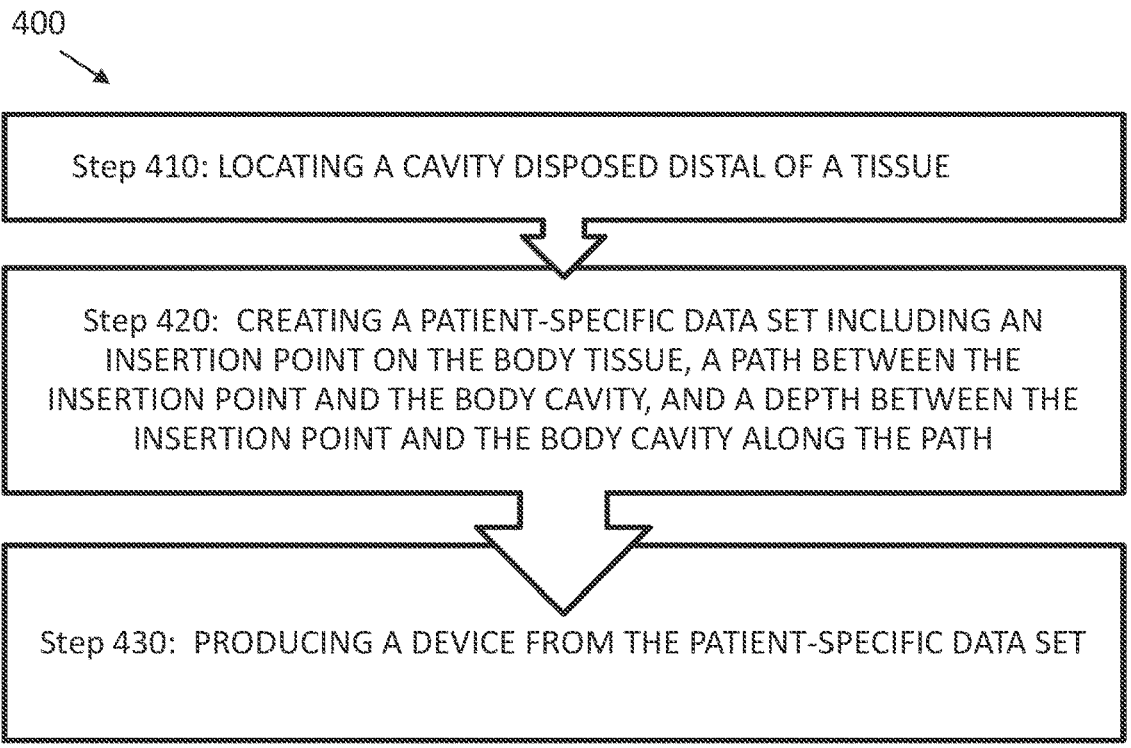
FIGS. 5A-B depict other exemplary methods according to this disclosure.
Figure 5B:
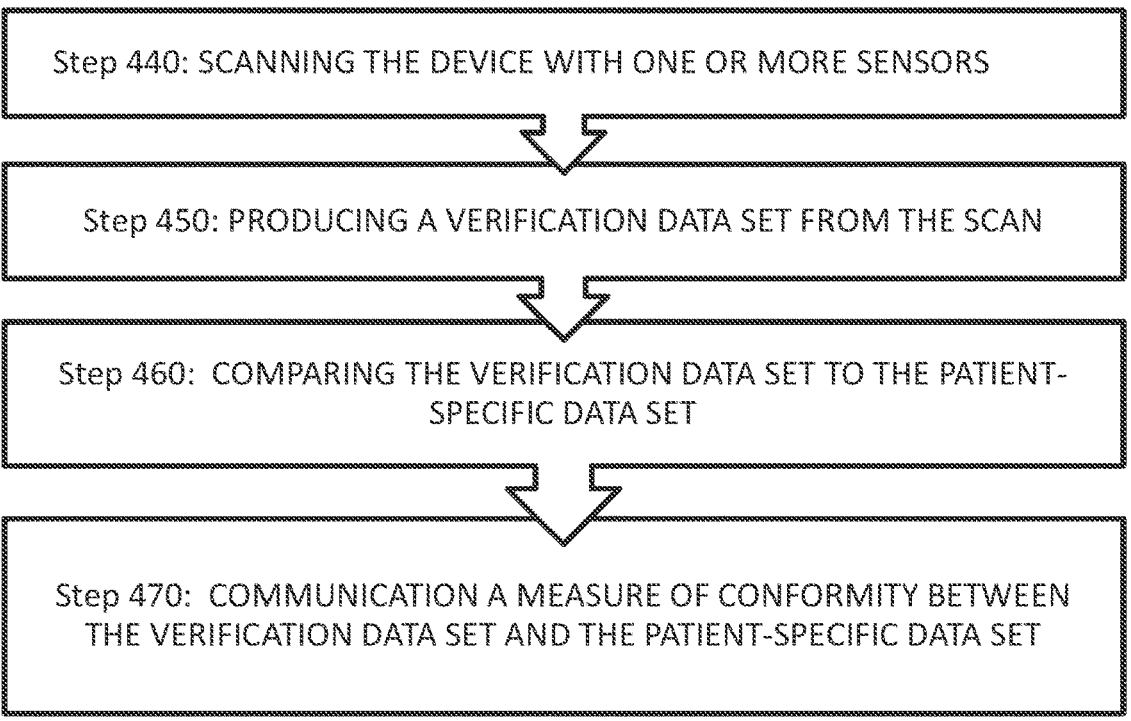
Figure 7:
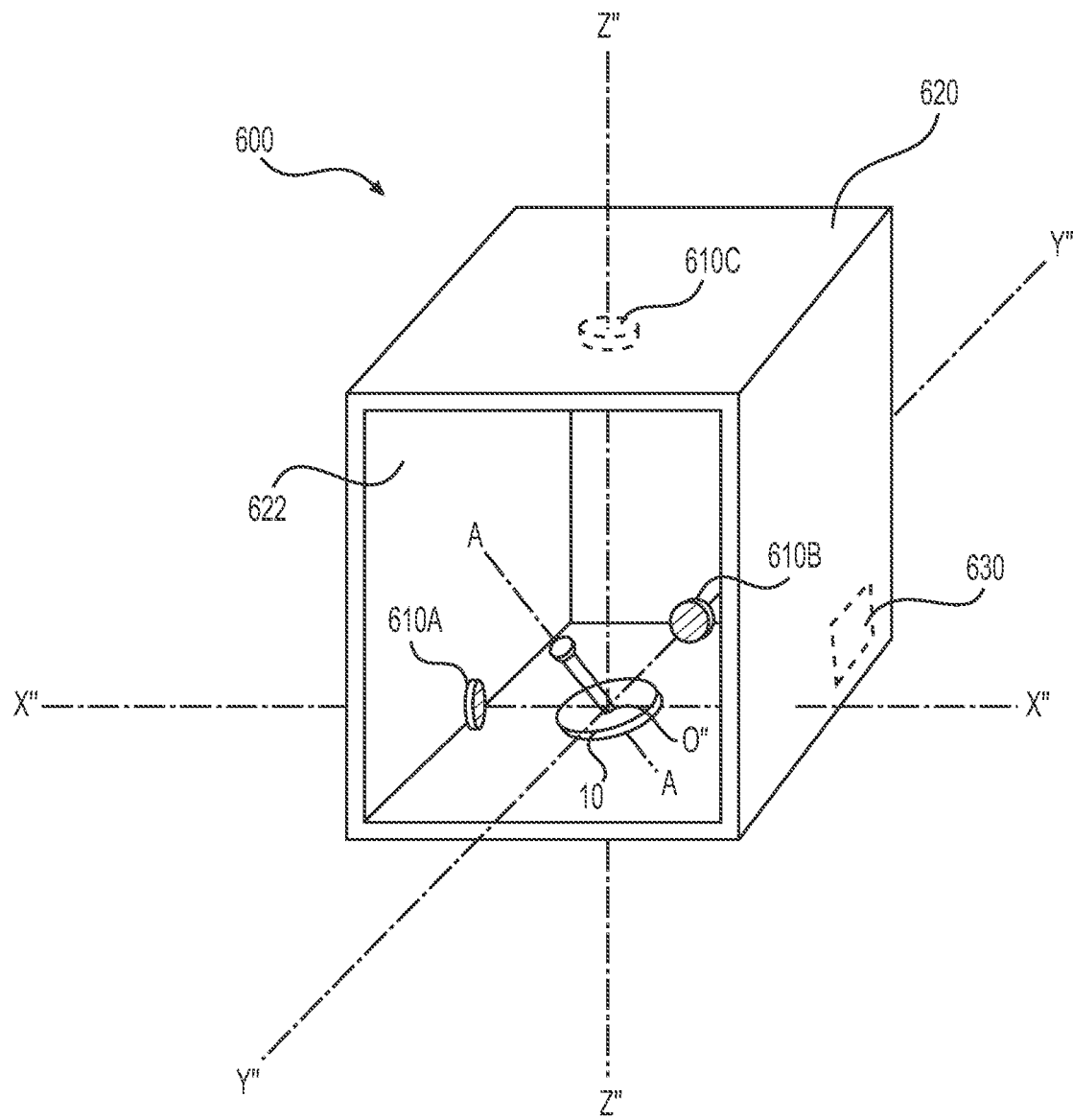
FIG. 7 depicts a perspective view of an exemplary verification device according to this disclosure.

Device 600 of FIG. 7 further includes at least one processor 630 configured to receive the geometric data; build the verification data set therefrom; compare the verification data set with the patient-specific data set used to produce device 10; and determine a measure of conformity between the two data sets. For example, as shown in FIG. 5B, if device 10 is produced in method 400 using the patient specific data set, then method 400 may further comprise scanning device 10 with transducers 610A-C (440); producing verification data set from the scan (450); comparing the verification data set with the patient-specific data set (460); and communicating a measure of conformity therebetween (470), such as an output signal or report indicating that the actual geometry of device 10 conforms with the patient-specific data set.

Device 600 may be a stand-alone device, as shown in FIG. 7. Alternatively, the first, second, and third ultrasound transducers 610A-C may be mounted in the production bay of a 3D printer. For example, each transducer 610A-C may be mounted on an adhesive or magnetic backing, allowing sensors 610A-C to be added onto the housing and/or positioned therein. In some aspects, the 3D printer may be configured to print device 10 so that the respective origin points O, O', and O" are aligned during production, allowing transducers 610A-C to be used for immediate verification.

While principles of the present disclosure are described herein with reference to illustrative aspects for particular applications, the disclosure is not limited thereto. Those having ordinary skill in the art and access to the teachings provided herein will recognize additional modifications, applications, aspects, and substitution of equivalents all fall in the scope of the aspects described herein. Accordingly, the present disclosure is not to be considered as limited by the foregoing description.

The invention claimed is:

1. A device comprising:
   a needle guide body extending along a central axis between a distal end and a proximal end,
   a needle guide lumen extending through the distal and proximal ends of the needle guide body along the central axis, and
   a base monolithically attached to the needle guide body to define a non-variable patient-specific insertion path, wherein the needle guide body is removably attached to the base via the distal end of the needle guide body,
   a sheath guide body extending along the central axis between a distal end and a proximal end, and
   a sheath guide lumen extending through the distal and proximal ends of the sheath guide body along the central axis, wherein a size of the sheath guide lumen is approximate to the one or more dimensions of a sheath, the needle guide lumen is contained with the sheath guide lumen, and the distal end of the sheath guide body is attached to the base
   wherein the needle guide body, the needle guide lumen, the base, the sheath guide body, and the sheath guide lumen are created using a patient-specific data set.

2. The device of claim 1, wherein the needle guide body is removably attached to the base via the distal end of the needle guide body by one or more frangible portions.

3. The device of claim 1, wherein the proximal end of the needle guide body is offset from the base along the central axis by a patient-specific depth.

4. The device of claim 1, wherein the proximal end of the needle guide body is configured to guide a tip of a needle into the needle guide lumen.

5. The device of claim 1, wherein a distal surface of the base includes patient-specific contouring.

6. The device of claim 1, wherein a perimeter of the base includes one or more elements configured to retain a portion of a guidewire.

7. The device of claim 1, wherein the sheath guide body is divided into a plurality of sheath guide walls arranged about the central axis.

8. The device of claim 7, wherein the sheath guide body is engageable with a distal end of the sheath so that an exterior diameter of the sheath is coaxial with the central axis.

9. A method comprising:
positioning a base of a device against a tissue, the device including a needle guide body extending along a central axis between a distal end and a proximal end, and a needle guide lumen extending through the distal and proximal ends of the needle guide body along the central axis, wherein the needle guide body is attached to the base;
attaching the base to the tissue so as to maintain alignment of the central axis with a non-variable patient-specific insertion path through the tissue;
moving a needle distally through the needle guide lumen in order to penetrate the tissue along the non-variable patient-specific insertion path, wherein the needle has a needle lumen extending therethrough;
moving a guidewire distally through the needle lumen until at least a distal end of the guidewire is located in a cavity;
detaching the needle guide body from the base by removing the distal end of the needle guide body from the base, wherein the needle guide body is removably attached to the base and the needle guide body is detached from the base without removing the distal end of the guidewire from the cavity;
moving the needle proximally along the guidewire without removing the distal end of the guidewire from the cavity; and
removing the needle from the cavity.

10. The method of claim 9, further comprising moving the needle distally through the needle guide lumen by a patient-specific depth.

11. The method of claim 9, wherein the device further includes a sheath guide body extending along the central axis between a distal end and a proximal end, and a sheath guide lumen extending through the distal and proximal ends of the sheath guide body along the central axis, wherein the needle guide lumen is contained within the sheath guide lumen, and the distal end of the sheath guide body is attached to the base, the method further comprising:
threading a proximal end of the guidewire through a sheath lumen extending through a sheath;
moving the sheath distally along the guidewire until a distal end of the sheath is engaged with the sheath guide lumen and an exterior diameter of the sheath is coaxial with the central axis; and
removing the guidewire from the body through the sheath lumen.

12. The method of claim 9, further comprising:
after detaching the needle guide body from the base, moving a proximal end of the guidewire through a sheath lumen extending through a sheath; and
moving the sheath distally along the guide wire until a distal end of the sheath is engaged with a sheath guide body and an exterior diameter of the sheath is coaxial with central axis.

13. The method of claim 12, further comprising removing the guidewire from the cavity through the sheath lumen.

14. The method of claim 12, further comprising moving an elongated device into the cavity along the non-variable patient-specific insertion path through the sheath lumen.

15. A method comprising:
creating a patient-specific data set including one or more dimensions of a sheath, an insertion point on a body, a insertion path between the insertion point and a cavity of the body, and an insertion depth between the insertion point and the cavity along the insertion path; and
producing a device from the data set, the device including:
a needle guide body extending along a central axis between a distal end and a proximal end,
a needle guide lumen extending through the distal and proximal ends of the needle guide body along the central axis,
a base monolithically attached to the needle guide body to define a non-variable patient-specific insertion path, wherein a distal end of the needle guide body is removable from the base,
a sheath guide body extending along the central axis between a distal end and a proximal end, and
a sheath guide lumen extending through the distal and proximal ends of the sheath guide body along the central axis,
wherein a size of the sheath guide lumen is approximate to the one or more dimensions of the sheath, the needle guide lumen is contained with the sheath guide lumen, and the distal end of the sheath guide body is attached to the base.

16. The method of claim 15, wherein the patient-specific data includes a topography of a surface contour on the tissue at the insertion point, and the device is produced to include a patient-specific contouring that corresponds with the topography.

17. The method of claim 15, wherein the patient-specific data includes one or more dimensions of a needle, and the device is produced to include a needle stop surface offset from the base by a distance approximate to the one or more dimensions of the needle.

18. The method of claim 15, wherein producing the device comprises printing the device with a 3D printer, and the method further comprises:
positioning the base of the device against a tissue;
attaching the base to the tissue to maintain alignment of the central axis with the patient-specific insertion path; and
moving a needle distally through the needle guide lumen in order to penetrate the tissue along the patient-specific insertion path.

19. The method of claim 15, wherein the patient-specific data set further includes an insertion angle, and the insertion angle and the insertion depth are determined by locating a series of points on a tissue.

20. The method of claim 15, wherein the sheath guide body is cylindrical.

* * * * *